US 6,731,827 B2

(12) United States Patent  (10) Patent No.: US 6,731,827 B2
Lackhart  (45) Date of Patent: May 4, 2004

(54) POLARIZATION-SENSITIVE COUPLED FIBER-OPTIC BIOSENSOR

(75) Inventor: Michael D. Lackhart, Charlottesville, VA (US)

(73) Assignee: Veridan Systems Division, Ann Arbor, MI (US)

( * ) Notice: Subject to any disclaimer, the term of this patent is extended or adjusted under 35 U.S.C. 154(b) by 230 days.

(21) Appl. No.: 10/093,335

(22) Filed: Mar. 7, 2002

(65) Prior Publication Data

US 2002/0126938 A1 Sep. 12, 2002

Related U.S. Application Data

(60) Provisional application No. 60/273,962, filed on Mar. 7, 2001.

(51) Int. Cl.$^7$ .............................. G02B 6/26; G02B 6/27
(52) U.S. Cl. ............................. 385/12; 385/11; 385/43
(58) Field of Search ............................. 385/11, 12, 27, 385/30, 39, 41–43

(56) References Cited

U.S. PATENT DOCUMENTS 5,494,798 A * 2/1996 Gerdt et al. ................... 435/6

FOREIGN PATENT DOCUMENTS

EP          722081 A2 * 7/1996 ............ G01D/5/26

* cited by examiner

Primary Examiner—John D. Lee
Assistant Examiner—Sarah Song
(74) Attorney, Agent, or Firm—Gifford, Krass, Groh, Sprinkle, Anderson & Citkowski, PC

(57) ABSTRACT

Coupled fiber-optic, evanescent-wave biosensors are improved through the use of configurations which detect changes in polarization for enhanced sensitivity. The inventive approach forms the necked-down region by heating and pulling the fibers without twisting them. As such, when polarized light is introduced, including randomly polarized light, the outputs will exhibit a split based upon polarization orientation as well. One or more bindings partners are then attached to the necked-down region and within the evanescent field for very specific and direct detection of minute concentrations of an analyte of interest. The invention is applicable to any type of organic/inorganic material, so long as the interaction of one component causes a change in any optical property detectable by the apparatus. The biomolecule may be linked to the surface of the fusion joint by means of a spacer molecule. Polarizing beam splitters are employed to detect the based upon polarization orientation.

7 Claims, 3 Drawing Sheets

POLARIZATION-SENSITIVE COUPLED FIBER-OPTIC BIOSENSOR

REFERENCE TO RELATED APPLICATION

This application claims priority from U.S. provisional patent application Ser. No. 60/273,962, filed Mar. 7, 2001, the entire contents of which is incorporated herein by reference.

FIELD OF THE INVENTION

This invention relates generally to fiber-optic, evanescent-wave biosensors and, in particular, to such a sensor that takes advantage of information derived from polarization orientation.

BACKGROUND OF THE INVENTION

Optical fibers are being used in a variety of sensor applications. For example, as discussed in U.S. Pat. No. 5,494,798, a pair of optical fibers may be pulled into a fused biconical coupler and used without cladding to exploit the evanescent field present immediately outside the fiber coupler waist/air interface. If an antibody is attached to the exposed surface of the bare fiber, the evanescent field envelopes the molecule.

When an antigen subsequently attaches to the antibody, there are changes in the evanescent field can force a shift in the output coupling ratio. This results in an optically detectable characteristic signal.

Whereas previous fiber-optic evanescent-wave sensors utilized multi-mode fibers, the '798 patent improved on the technique by employing a pair of single-mode optical fibers in a coupler arrangement. Light is introduced into one of the fibers to produce an evanescent region surrounding the coupling area, and the magnitude of light emitted from the pair of fibers is compared for detection purposes.

FIG. 1, taken from the '798 patent, shows the overall fiber optic system generally at 10. Light from laser diode 14 is inserted into a first leg 17 of a fiber optic coupler 18, and exits on the same fiber at 19 (input channel). A second fiber 20 provides an output channel for light from the first leg 17. A first photo diode detector 21 is connected to the input channel and a second photo diode detector 22 is connected to the output channel.

Each detector feeds its own transimpedance amplifier. The outputs of the transimpedance amplifiers 23, 24 are applied to A/D converters 25 and 26 which provide digital electrical signals along wires 27 and 28 to an instrumentation board 29. The instrumentation board 29 is then connected to a personal computer 30 which provides outputs to a printer or a monitor.

The finished probe includes the coupler and attached antibodies, which yields a baseline ratio for the sensor. The finished probe is then exposed to a material of interest, and the ratio of the light through the two sides of the coupler changes as a function of the way in which the target attaches. That is, the localized index of refraction at the coupling region and the determination of the ratio is a function of the binding in the coupler region.

FIG. 2 is a graph which shows how index of refraction changes when the coupling region is immersed in solution and the antibodies attach. Note that the system is most efficient when the baseline ratio is on the steep portion of a curve as opposed to a local maximum or minimum. That is, it is best to operate at point 'X' as opposed to, say, point 'Y.' By operating on the steep initial slope of the curve, very few antigens will cause a significant shift in ratio which is more easily detected.

In terms of the coupler itself, existing designs use off-the-shelf components intended for multiplexers and demultiplexers in telecommunications applications. Corning, for instance, makes these couplers by twisting together two or more 1300-nm, single-mode type SMF 9-125 optical fibers, heating up the twisted area and pulling the ends apart to create a necked-down (waist), nearly fused region. The number of fibers and other factors such as the proportion of each fiber in the twisted region determines the coupling ratio.

SUMMARY OF THE INVENTION

This invention improves upon the art of coupled fiber-optic, evanescent-wave biosensors through the use of configurations which detect changes in polarization for enhanced sensitivity. In contrast to existing techniques, wherein the fibers are twisted while pulled to disrupt polarization orientation, the inventive approach forms the necked-down region by heating and pulling the fibers without twisting them. As such, when polarized light is introduced, including randomly polarized light, the outputs will exhibit a split based upon polarization orientation as well.

One or more optical devices are then used to detect this change in polarization. In the preferred embodiment, polarizing beam splitters are employed to detect the split based upon polarization orientation. For example, light having more P-polarized light may emerge through one fiber, whereas more S-polarized light may emerge from another. Although the split in polarization may not be 100%, a system according to the invention may be appropriately modified to adjust the ratio of P to S levels.

One or more bindings partners are then attached to the necked-down region and within the evanescent field for very specific and direct detection of minute concentrations of an analyte of interest. The invention is applicable to any type of organic/inorganic material, so long as the interaction of one component causes a change in any optical property detectable by the apparatus. Interactions to which the invention is applicable include, but are not limited to, antigen-antibody, carbohydrate-lectin, receptor-ligand, binding protein-toxin, substrate-enzyme, effector-enzyme, inhibitor-enzyme, complimentary nucleic acid strands, binding protein-vitamin, binding protein-nucleic acid, reactive dye-protein, and reactive dye-nucleic acid interactions. The biomolecule may be linked to the surface of the fusion joint by means of a spacer molecule. Although the invention assumes the use of glass fibers, polymeric fibers may also be used in certain situations.

DETAILED DESCRIPTION OF THE INVENTION

Although the basic concept of a fiber-optic coupler as presented in U.S. Pat. No. 5,494,798 is useful in the detection of certain biologic substances, the approach could be made more sensitive by paying further attention to the coupler itself and by sensing additional optical parameters. This invention is directed to such improvements, with the goal or achieving, in some cases, orders of magnitude in detection sensitivity.

In broad and general terms, whereas the telecommunications industry desires perfect optical fiber and other elements to realize many miles of uninterrupted service and no degradation of signal, an important goal of this invention is to introduce and exploit intentional discontinuities in the optical system in an effort to maximize sensitivity.

While the system of the '798 patent uses a ratio of light to enhance sensitivity, is evident from the teachings of the patent that the system relies only on the ratio of light intensity or magnitude, and does not consider other optical properties. For example, in using commercially available components, it is clear that the '798 patent does not take polarization into account.

The couplers provided for telecommunications applications are intentionally designed to be insensitive to polarization in order achieve high gigabyte data rates with low error rates. When conventional couplers are twisted together, polarization is scrambled, thereby limiting the method to a direct ratio which cannot include any advantages to be gained from detecting changes in polarization.

Figure 1:
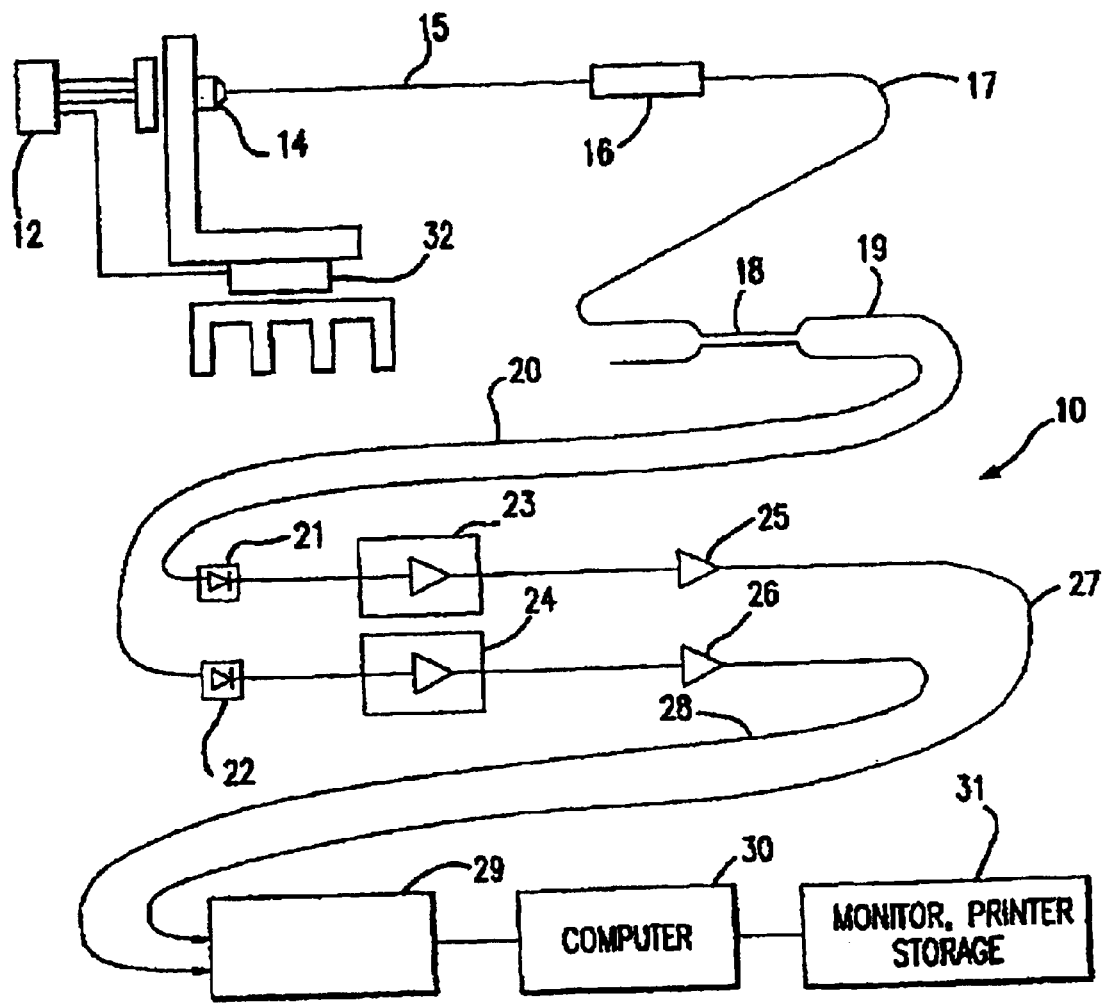
FIG. 1 is a diagram which illustrates a prior-art coupled-fiber evanescent wave biosensor configuration.
Figure 2:
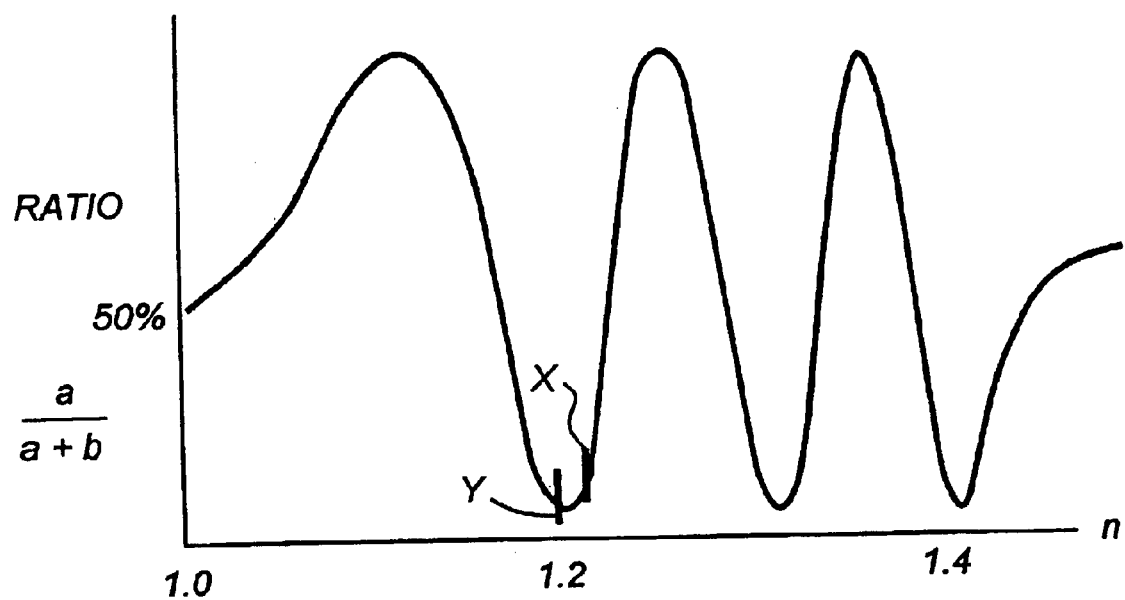
FIG. 2 is a graph which shows how index of refraction changes when the coupled region introduced with respect to FIG. 1 is immersed in solution with antibodies attached thereto.
Figure 3A:
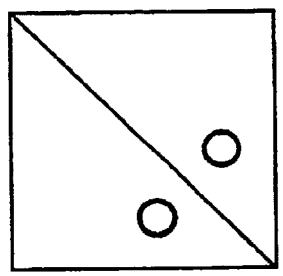
FIG. 3A is a drawing associated with a commercially available beamsplitter, wherein the axes of polarization are aligned or parallel to one another.
Figure 3B:
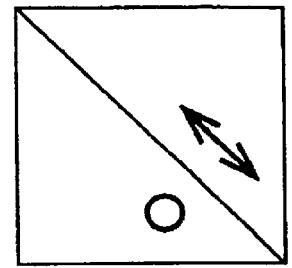
FIG. 3B is a drawing of a commercially available beamsplitter wherein the axes of polarization are orthogonal to one another.

FIGS. 3A and 3B are drawings of commercially available beam splitters. A dot indicates that the axis of the polarization is into the page, whereas the double-headed arrow is used to indicate that the orientation of the axis of the quartz material is parallel to the page. In FIG. 3A, the axes are aligned or parallel to one another; whereas in FIG. 3B the axes are orthogonal.

Figure 4A:
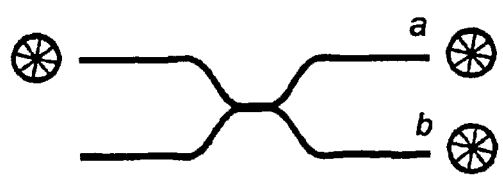
FIG. 4A is a diagram used to show how randomly polarized light introduced into a conventional fiber optical coupler as randomly polarized light is also output as randomly polarized light.

FIG. 4A is used to illustrate that when one introduces randomly polarized light into a conventional fiber-optic coupler, the output is randomly polarized as well. For this reason, only the change in the ratio of light intensity may be used for detection purposes.

Figure 4B:
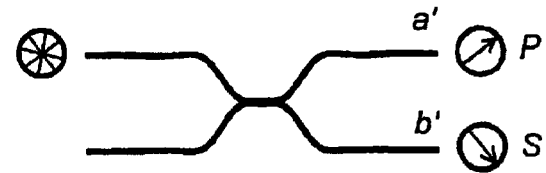
FIG. 4B is a coupler arrangement used to introduce two improvements afforded by the instant invention, namely, a coupler which is formed by heating and pulling without twisting and the use of beamsplitters of the type disclosed with reference to FIGS. 3A and 3B to detect polarization orientation.

The coupler arrangement of FIG. 4B includes two improvements according to the invention. First, the coupler is formed by heating and pulling the fibers without twisting them. As such, when randomly polarized light is introduced, the outputs will depend not only on a change in magnitude, but there will be a split based upon polarization orientation as well. Secondly, optical elements such as the polarizing beam splitters depicted in FIGS. 3A and 3B are used at the outputs of the fibers to detect the split based upon polarization orientation. For example, light having more P-polarized light may emerge at the top fiber, whereas more S-polarized light may emerge at the bottom.

Figure 5:
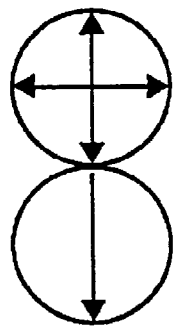
FIG. 5 is a simplified diagram which illustrates how output polarization may be segregated based upon orientation.

An end-view output of the coupler is shown in FIG. 5. Although the split in polarization may not be 100 percent, a system according to the invention may be appropriately modified such that "up-and-down" polarized light is more likely to enter the lower fiber whereas the "side-to-side" polarized light is more likely to remain in the upper fiber. In any case, the result will be a split in the output based upon polarization.

Now, when one changes the index at the coupling region, a change in the affinity to a particular polarization orientation at the output is seen as well. These outputs are labeled "a" and "b" in FIG. 4A, and a' and b' in FIG. 4B. When considering polarization, one can use the relation:

$$Xa'=Xa+Pa'$$

where $Xa$ is the ratio of light intensity without taking polarization into account, and $Pa'$ is an additional increment gained from considering the contribution of polarization.

Figure 6:
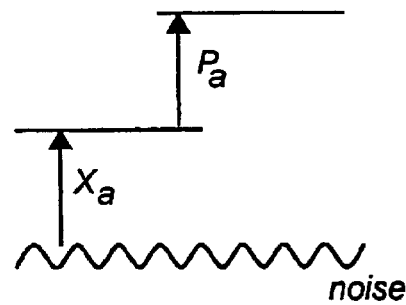
FIG. 6 is a simplified diagram which helps to visualize how, through the use of polarization, the signal-to-noise ratio may be improved.

Reference is now made to FIG. 6. Given that the noise is the same whether or not polarization is considered, an additional increment of $Pa'$ is realized through sensing the orientation of the polarization. Moreover, although this advantage is present with a non-polarized input, an intentionally polarized input may alternatively be used to look for a particular ratio based upon polarization orientation. In this way, one may achieve a near-digital output in accordance with a particular target or material of interest.

Applications

This invention provides a sensitive detector having a wide variety of applications in the fields of biology, biochemistry and chemistry, and in many clinical applications. Although the terms "antigen" and "antibody" are used herein, it will be appreciated that is a special case, and that the invention finds utility beyond the more general target-specific molecular recognition. Indeed, the invention is applicable to both direct types of lock-and-key molecular recognition and indirect mechanisms, for example, subclasses of carbohydrates that are based upon more of a pattern match than a precise attachment mechanism.

In broad and general terms, the invention sense a change in one or more optical properties due to chemical/biochemical/bioaffinity/immunogenic-type interactions of biomolecules (ligands) with their respective binding partners. The terms ligand and its binding partner for the ligand or, simply, binder will be used to represent the two components in specific bioaffinity binding pairs, all of which are capable of recognizing and binding with the other partner in a bimolecular recognition pair. References to "biomolecular" or "molecular constituent," "binding partner," and so forth are used interchangeably and are not intended to in any way limit the invention, since the invention is applicable to any type of organic/inorganic material, so long as the interaction of one component causes a change in any optical property detectable by the apparatus. Interactions to which the invention is applicable include, but are not limited to, antigen-antibody, carbohydrate-lectin, receptor-ligand, binding protein-toxin, substrate-enzyme, effector-enzyme, inhibitor-enzyme, complimentary nucleic acid strands, binding protein-vitamin, binding protein-nucleic acid, reactive dye-protein, and reactive dye-nucleic acid interactions.

A molecular constituent useful in the present invention is characterized by an ability to specifically interact with another molecule, the interaction resulting in a change in an optically detectable property. A molecular constituent is any molecule, or portion of a molecule, that is capable of being attached, directly or indirectly to a waveguide such that it is capable of specific interaction with another molecule present in a test sample. Examples of a molecular constituent illustratively include a protein, a peptide, a polysaccharide, a sugar, an antibody, an antigen, a hapten, a receptor, a ligand such as an agonist or antagonist, a sugar binding protein such as a lectin, a toxin, a virus, a bacterium, a cell, a cell component such as an organelle, a particle such as a liposome, a nucleic acid, a drug and a prion. A molecular constituent further includes fragments or metabolites of the listed substances capable of specific interaction as described. Further, a molecule interacting with another molecule of the present invention is a gas illustratively including NO, $O_2$, $CO_2$. A molecular constituent also illustratively includes a chemical-sensitive polymer, a chemical-sensitive microimprinted polymer and a chemical-sensitive dye.

The terms "interaction" and "binding" are used interchangeably herein and refer to a selective association, through chemical or physical means, of two or more molecules. By "selective association" is meant that a first molecule binds preferentially to a second molecule or with greater affinity than to most other molecules. For example, a DNA molecule will selectively associate with a substantially complementary sequence and not with unrelated nucleic acids.

A test sample containing a molecular constituent to be detected is typically a biological sample. A biological sample is obtained from a human or other animal or from an environmental site where the earth, water or air are to be tested. Environmental sites include outdoor locations as well as indoor location such as laboratories, hospitals and manufacturing facilities. A sample illustratively refers to a cells, tissue or physiological fluid, such as plasma, serum, cerebrospinal fluid, saliva, semen, amniotic fluid, tears, milk, and fluids obtained from respiratory, upper digestive, intestinal, and genitourinary tracts. A test sample also includes fluid or a suspension of solids obtained from wounds, tumors and organs. Further, a test sample is obtained to test for environmental contamination. For example, a surface suspected to be contaminated by bacteria is swabbed and the bacteria obtained are suspended in a solution for later introduction into a biosensor of the present invention.

In one embodiment of the present invention, the interaction of molecular constituents acts to cleave or release molecules attached to the waveguide. For example, a substrate is attached to a waveguide and an enzyme to be detected interacts with the substrate under appropriate conditions. The resulting enzyme activity cleaves the substrate causing a change in an optical property.

In an embodiment of the instant invention, the interaction of molecular constituents results in the formation of another molecular species such that a change in an optical property is detected. For example, an enzyme interacts with a substrate to produce a product deposited on or near the waveguide such that a change in an optical property is detected. Techniques of enzymatic reaction are well known in the art. A preferred example is horseradish peroxidase used in conjunction with diaminobenzidine and $H_2O_2$ or a similar substrate such as tetramethylbenzidine or aminoethylcarbazole.

The term "attached" as used herein to describe the relationship of a first molecular constituent with a waveguide is intended to mean attached either directly or indirectly to the waveguide. An illustrative example of a direct attachment is a link to a pendant moiety on a waveguide via a pendant chemical moiety present on the first molecular constituent. An indirect attachment occurs, for example, where a molecular constituent is optionally attached to a waveguide via a linker. Where a linker is used the choice of linker depends on the surface of the waveguide and the molecular constituent to be attached. Selection of an appropriate combination will be evident to one skilled in the art. For example, where the surface has available Si—OH groups, appropriate linkers include aminoalkyltrialkoxysilanes, aminoalkyltrichlorosilanes, carboxyalkyltrialkoxysilanes, epoxyalkyltrialkoxysilanes, hydroxyalkyltrialkoxysilanes and hydroxyalkyltrichlorosilanes. Further suitable silanes are listed in Silicon Compounds: Register & Review, from United Chemical Technologies, 5th Ed., 1991. Further illustrative examples of linkers include aryl acetylene, diamines, diacids, polyalcohols, polyesters, polyethers, polylysine, polyarginine, polystyrene sulfonate, dextran sulfate, chondroitin, polyacrylic acid, polymethacrylic acid, polyacrylamide, polyallylamine, maleic acid, substituted or unsubstituted polyalkylenes, polyamines, polyamides, polysufonates, polyoxides, polyalkyleneglycols, polystyrenic-based polymers, polyacetals, polysaccharides, polycarbonates, polyurethanes, polyureas, polyamides, polyethyleneimines, polyarylene sulfides, polysiloxanes, polyimides, polyacetates, polymers of monoethylenically unsaturated monomers, polymers of polyvinylidene monomers and mixtures and copolymers of the above polymers. Following linker binding, unreacted functional groups on the waveguide surface are optionally blocked to prevent further reaction.

It will be appreciated by one skilled in the art that a molecular constituent attached to a waveguide is removable according to the mechanism of attachment used. Thus, a wave guide according to the invention is reusable.

An apparatus of the present invention allows detection of a molecular constituent in a test sample where the concentration of the constituent is in the range of $10^{-3}$ M to $10^{-15}$ M or less. Sensitivity of the apparatus will depend in part on the amount and concentration of the constituent attached to the waveguide.

Substances are optionally introduced into the cavity 140 to facilitate an interaction between molecular constituents. For example, a gel is introduced into the cavity. Gels operative in the present invention are any that do not interfere with the desired interaction and illustratively include agarose and acrylamide. The viscosity of a gel is chosen such that a molecular constituent in a sample to be tested remains in the cavity available for interaction with the waveguide attached molecular constituent for an appropriate period of time which is apparent to one of skill in the art.

It will be readily apparent to one of skill in the art that specific interaction between molecular constituents is to some extent dependent on appropriate interaction conditions such as temperature, salt concentration and buffer composition. Solutions used in a biosensor apparatus of the present invention are adjusted according to the desired interaction. An apparatus of the present invention optionally has a thermostatic control for regulating the temperature at which the molecular constituents are brought into contact.

The interaction of molecular constituents causing a change in an optical property is not limited to the interaction of two constituents. Thus, interaction of three or more molecules may be required to cause an optical change. For example, an antibody attached to a waveguide interacts with an antigen to be detected resulting in minimal or undetectable change in an optical property. A third molecular constituent, such as an antibody interacts with the antigen-antibody complex to bring about a change in an optical property.

As a final note, although the invention assumes the use of glass fibers, polymeric fibers and other materials may be used, depending upon the wavelengths of interest or other aspects of the particular analytical configuration. Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

I claim:

1. An optical biosensor, comprising:
    a fiber-optic coupler incorporating at least two optical fibers, each fiber having an input and an output;
    a source of light having a polarization orientation coupled to at least one of the inputs;
    the coupler including a necked-down section around which an evanescent field is generated when the light passes through with the polarization orientation being substantially maintained;
    a biomolecule enveloped by the evanescent field, the biomolecule exhibiting a direct or indirect affinity to a binding partner, such that attachment of the binding partner causes a change in the polarization orientation of the light at one or both of the fiber outputs; and
    instrumentation for receiving the light from the fiber outputs and for determining a characteristic of the binding partner in accordance with the change in the magnitude and polarization orientation.

2. The optical biosensor of claim 1, wherein the biomolecule and binding partner include one or more of the following:
    antigen-antibody,
    substrate-enzyme,
    effector-enzyme,
    inhibitor-enzyme,
    complimentary nucleic acid strands,
    binding protein-vitamin,
    binding protein-nucleic acid,
    reactive dye-protein, and
    reactive dye-nucleic acid interactions.

3. The optical biosensor of claim 1, wherein the instrumentation includes a polarization-sensitive optical element supported at one or both of the outputs of the optical fibers.

4. The optical biosensor of claim 3, including a polarization-sensitive optical element in the form of a polarizing beamsplitter.

5. The optical biosensor of claim 1, wherein attachment of the binding partner also causes a change in magnitude of the light at one or both of the fiber outputs.

6. The optical biosensor of claim 1, wherein:
    the necked-down section is produced by pulling the optical fibers; and
    wherein one or more of the fibers are pulled substantially without twisting so as to maintain polarization orientation.

7. The optical biosensor of claim 1, wherein the source of light is randomly polarized.

* * * * *

UNITED STATES PATENT AND TRADEMARK OFFICE
CERTIFICATE OF CORRECTION

PATENT NO. : 6,731,827 B2
DATED : May 4, 2004
INVENTOR(S) : Michael D. Lockhart

It is certified that error appears in the above-identified patent and that said Letters Patent is hereby corrected as shown below:

Title page,
Item [75], Inventor, replace "Michael D. Lackhart" with -- Michael D. Lockhart --.

Colulmn 3,
Line 44, replace "order achieve" with -- order to achieve --.

Signed and Sealed this

Twenty-third Day of November, 2004

JON W. DUDAS
*Director of the United States Patent and Trademark Office*